(12) United States Patent
Lalonde et al.

(10) Patent No.: US 6,589,234 B2
(45) Date of Patent: Jul. 8, 2003

(54) CRYOGENIC MEDICAL DEVICE WITH HIGH PRESSURE RESISTANCE TIP

(75) Inventors: Jean-Pierre Lalonde, Verdun (CA); Marwan Abboud, Pierrefonds (CA); Constantin Bogdan Ciobotaru, Lasalle (CA)

(73) Assignee: CryoCath Technologies Inc., Kirkland (CA)

(*) Notice: Subject to any disclaimer, the term of this patent is extended or adjusted under 35 U.S.C. 154(b) by 0 days.

(21) Appl. No.: 09/965,208

(22) Filed: Sep. 27, 2001

(65) Prior Publication Data

US 2003/0060815 A1 Mar. 27, 2003

(51) Int. Cl.[7] ............................................... A61B 18/18
(52) U.S. Cl. ........................... 606/23; 606/20; 606/21; 607/104; 607/105
(58) Field of Search ................. 606/20, 26; 607/96, 607/104, 105

(56) References Cited

U.S. PATENT DOCUMENTS

| | | | |
|---|---|---|---|
| 3,425,419 A | 2/1969 | Dato | 128/400 |
| 3,859,986 A | 1/1975 | Okada et al. | 128/7 |
| 3,948,269 A | 4/1976 | Zimmer | 128/303 |
| 4,946,460 A | 8/1990 | Merry et al. | 606/24 |
| 5,078,713 A | 1/1992 | Varney | 606/23 |
| 5,211,646 A | 5/1993 | Alperovich et al. | 606/23 |
| 5,275,595 A | 1/1994 | Dobak, III | 606/23 |
| 5,281,213 A | 1/1994 | Milder et al. | 606/15 |
| 5,281,215 A | 1/1994 | Milder | 606/20 |
| 5,324,286 A | 6/1994 | Fowle | 606/23 |
| 5,403,309 A | 4/1995 | Coleman et al. | 606/20 |
| 5,423,807 A | 6/1995 | Milder | 606/20 |
| 5,520,682 A * | 5/1996 | Baust et al. | 606/24 |
| 5,573,532 A | 11/1996 | Chang et al. | 606/26 |
| 5,624,392 A | 4/1997 | Saab | 604/43 |
| 5,716,353 A | 2/1998 | Matsuura et al. | 606/22 |
| 5,759,182 A | 6/1998 | Varney et al. | 606/21 |
| 5,800,487 A | 9/1998 | Mikus et al. | 607/105 |
| 5,800,488 A | 9/1998 | Crockett | 607/105 |
| 5,833,685 A | 11/1998 | Tortal et al. | 606/23 |
| 5,860,970 A | 1/1999 | Goddard et al. | 606/23 |
| 5,885,276 A | 3/1999 | Ammar et al. | |
| 5,992,158 A | 11/1999 | Goddard et al. | |
| 6,319,248 B1 * | 11/2001 | Nahon | 606/22 |

FOREIGN PATENT DOCUMENTS

| | | |
|---|---|---|
| EP | 1 129 670 A1 | 9/2001 |
| WO | WO 83/03961 | 11/1983 |

* cited by examiner

Primary Examiner—Rosiland S. Kearney
(74) Attorney, Agent, or Firm—Christopher & Weisberg, P.A.

(57) ABSTRACT

The present invention provides a medical device to cold treat desired regions. An injection tube with an open distal end is disposed inside of a catheter tube, defining a return lumen therein. A supply of cryogenic fluid, regulated by a controller mechanism coupled to the device, flows through the injection tube and into the distal tip portion of the catheter tube, whereupon the fluid is returned from the catheter through the return lumen. The expansion and evaporation of cryogenic fluid inside the device serves to cool the surrounding areas external to and proximate the distal end of the device. An additional restriction tube is provided in the length of the catheter tube to regulate the pressure of the flow of cryogen therethrough so as to create higher operating pressures in the distal end of the device and thereby enhance the cooling power and temperature stability of the device at a lower range of fluid flow rates without reaching the triple point of the cryogenic fluid.

18 Claims, 1 Drawing Sheet

CRYOGENIC MEDICAL DEVICE WITH HIGH PRESSURE RESISTANCE TIP

CROSS-REFERENCE TO RELATED APPLICATION

Not applicable.

STATEMENT REGARDING FEDERALLY SPONSORED RESEARCH OR DEVELOPMENT

Not applicable.

FIELD OF THE INVENTION

The present invention relates to medical devices, and in particular, to high pressure resistance mechanisms for devices which employ cryogenic fluids.

BACKGROUND OF THE INVENTION

Recently, the use of fluids with low operating temperatures, or cryogens, has begun to be explored in the medical and surgical field. Of particular interest are the potential use of catheter based devices, which employ the flow of cryogenic working fluids therein, to selectively freeze, or "cold-treat", targeted tissues within the body. Catheter based devices are desirable for various medical and surgical applications in that they are relatively non-invasive and allow for precise treatment of localized discrete tissues that are otherwise inaccessible.

A cryogenic device uses the energy transfer derived from thermodynamic changes occurring in the flow of a cryogen therethrough to create a net transfer of heat flow from the target tissue to the device, typically achieved by cooling a portion of the device to very low temperature through conductive and convective heat transfer between the cryogen and target tissue. The quality and magnitude of heat transfer is regulated by the device configuration and control of the cryogen flow regime within the device.

Structurally, cooling can be achieved through injection of high pressure cryogen through an orifice and subsequent expansion of the cryogen in an expansion chamber in the near-field of the orifice. For example, cryogen supplied at high pressure, ranging up to 800 psia, is generally a liquid-vapor mixture as it travels through a device to the orifice. Upon injection from the orifice, the cryogen undergoes two primary thermodynamic changes: (i) expanding to low pressure and temperature through positive Joule-Thomson throttling, and (ii) undergoing a phase change from liquid to vapor, thereby absorbing heat of vaporization. The resultant flow of low temperature cryogen through the expansion chamber acts to absorb heat from the target tissue proximate to the expansion chamber, and thereby cools the tissue to the desired temperature.

Of the two processes contributing to the cooling power of the device, evaporative boiling through a change in phase creates a far greater cooling effect through the absorption of latent heat of vaporization, on a specific basis, than that of Joule-Thomson cooling alone. Therefore, it is highly desirable to supply the device with a cryogen that is as much in liquid rather than gaseous phase, before the fluid is injected into the expansion chamber to cool tissue. However, during transit through the device, such as through an elongate catheter, the cryogen supplied typically passes through a region of comparatively high temperature, such as a region of the human body preceding the target area, and is thereby warmed. This warming, coupled with head losses in the flow of cryogen down a length of several hundred diameters of tubing, acts to degrade the quality of cryogen from its high pressure liquid form to a lower pressure, higher temperature, mixed phase form, leading to significantly degraded cooling power of the device.

Therefore, it is desirable to insulate the flow of cryogen as it is supplied from the proximal to the distal end of the device, so as to prevent the source cryogen from warming before it undergoes thermodynamic cooling.

Another problem presented in such a cooling process is that the cryogen vapor which rapidly cools in the expansion chamber may, if the resultant pressure drop is extreme enough, sublimate or precipitate if the pressure drops below that of the triple point for the cryogen. This sublimation naturally degrades the cooling power of the device, as heat transfer is drawn from the cryogen vapor into the cryogen particulate, rather than from the tissue proximate the device into the vapor. Worse, sublimation leads to unsteady flow, non-uniform density, and unstable temperature and non-equilibrium conditions. The sublimed particles may also block the flow of cryogen in the relatively small lumens, thereby creating dangerous high pressure conditions in the tip.

The cooling power of the device is directly related to the temperature drop in the expansion chamber, which is in turn a function of the pressure drop in the expansion chamber. While it is therefore desirable to reduce the pressure of the expanding cryogen as much as possible so as to benefit from the corresponding gas-dynamic cooling thereby created, care must be taken to avoid dropping the pressure below the triple point. Thus, it is desirable to create conditions in the expansion chamber where a maximum amount of cryogen flow is expanded to the lowest possible temperature, but at a pressure above the triple point. This may be most practically achieved by regulating the "back pressure" of the device, i.e. by fine-tuning the pressure conditions downstream of the expansion chamber, so as to create a nominal pressure in the expansion chamber which is higher than the triple point of the cryogen flowing therethrough.

Furthermore, because the catheter based device is to be inserted into a body lumen or other internal region of the human body, the device must maintain a fluid seal, lest potentially damaging cryogen leak during application of the device. As enumerated above, the cooling power of the device is dependent on achieving the maximum flow of high pressure liquid phase cryogen through the device, so that the maximum possible cooling occurs in the expansion chamber. Because the cryogen is injected into the expansion chamber through a choked orifice, the resultant pressure of the cryogen flowing in the expansion chamber is positively correlated to the source pressure and flow rate of the supplied cryogen. Therefore, increasing the flow rate and pressure of the supplied cryogen correspondingly increases the pressure of the resultant cryogen flow in the expansion chamber.

To contain the cryogen in the expansion chamber, the structural properties of the device must be sufficient to properly seal the device and withstand the operating pressure of the cryogen flowing therein. Thus, the device must be optimally designed to provide for a maximum amount of cryogen flow while maintaining its structural integrity.

It is therefore desirable to provide a medical device which maximizes the cooling power of the flow of cryogenic fluid therethrough, namely through maintaining a steady, uniform supply of high pressure cryogen in liquid phase. It is also desirable to provide a medical device which minimizes cooling losses in the flow of cryogen as it is applied to tissue, as well as maximizing the ratio of the cooling power of the device versus its internal flow lumen diameter. Finally, it is desirable to provide a structurally sound expansion chamber with a maximum possible operating pressure, so that the maximum possible cooling may occur therein.

SUMMARY OF THE INVENTION

The invention discloses a cryogenic medical device with high pressure resistance tip, and a method for cooling the same.

In one embodiment of the invention, the medical device comprises a first member defining an injection lumen, a second member circumferentially disposed around the first member to define a return lumen therebetween. The return lumen has at least one cross-sectional area. A third member is disposed between the second member and the first member to define a restriction lumen between the third member and the first member. The restriction lumen has at least one cross-sectional area smaller than the at least one cross-sectional area of the return lumen. In another embodiment of the invention, the medical device comprises an elongate injection tube having a proximal end portion having at least one proximal orifice, and a distal end portion having at least one distal orifice, and an elongate catheter tube circumferentially disposed around the injection tube and defining a return lumen therebetween. The catheter tube has a distal end portion, the distal end portion being coupled to a thermally transmissive element, where the thermally transmissive element circumferentially encloses the distal end portion of the injection tube. A restriction tube is circumferentially disposed inside of the catheter tube and encloses a portion of the return lumen proximate the thermally transmissive element.

Finally, a method for cooling the cryogenic medical device is disclosed. The method includes the steps of: (i) providing a supply of cryogen at a pressure of at least two atmospheres absolute pressure in a storage container; (ii) fluidly connecting said supply of cryogen with a catheter having a first lumen inside of a second lumen, and a thermally transmissive element; (iii) providing a flow regulation system to dispense cryogen into the first lumen and to reduce the pressure in the second lumen to below one atmosphere absolute pressure; (iv) controllably injecting said supply of cryogen through the first lumen in proximity to the thermally transmissive element; and (v) providing a third lumen inside of the second lumen, the third lumen being proximal to the thermally transmissive element, the third lumen having a cross-sectional area smaller than the cross-sectional area of the second lumen.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

As used herein, the term "cryogen" or "cryogenic fluid" refers to a fluid substance with properties suitable for: (i) steady flow through ducts of small diameter, (ii) high pressure compression into liquid phase, and (iii) evaporation and expansion to gas phase at low temperatures, typically at saturation temperature or in the range of −10 to −130 degrees centigrade The cryogen may be any suitable, relatively inert "working fluid", such as nitrogen, nitrous oxide, or carbon dioxide, or refrigerants such as chlorodifluoromethane, ethyl alcohol, or Freon (a trademark of DuPont), or any number of other refrigerants or fluids with a high thermal energy transfer capacity and low boiling point, as are commonly known to those skilled in the art.

As used herein, the term "tube" refers to an elongate duct or conduit suitable for conveying a fluid. The tube may comprise any number of elements or members, and may have a varying range of properties and dimensions, such as length, thickness, and cross-sectional shape.

As used herein, for a particular region or space with fluid flowing therein, the term "downstream" refers to the relative spatial direction equivalent to the direction of the macroscopic flow of such fluid in such region or space.

Also as used herein, the term "catheter" refers to a medical device composed of any number of tubes and ancillary structures, for insertion into canals, vessels, passageways or other body cavities to permit the treatment of body tissue proximate to the catheter. A catheter may be constructed from a variety of suitable materials having a varying range of structural and thermal properties. It is understood that the particular structural, dimensional, and/or thermal properties of a catheter included in the present invention may considerably vary depending on the particular application of the device disclosed herein.

Figure 1:
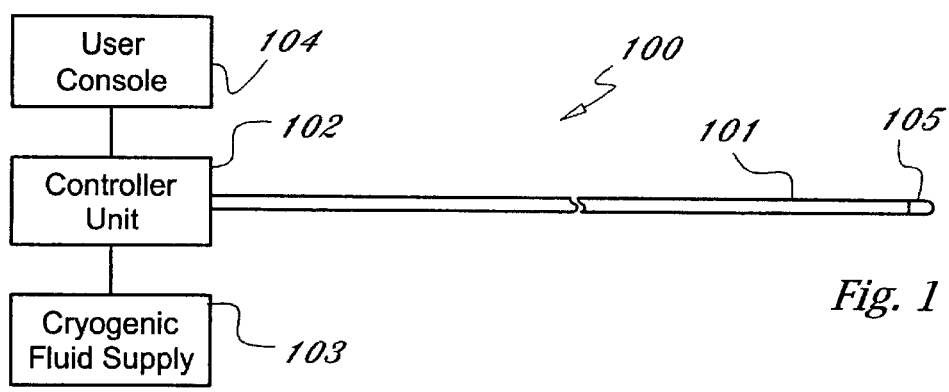
FIG. 1 is a schematic diagram of a system that includes a medical device in accordance with the present invention.

Referring now to the drawings, in which like reference designators refer to like elements, there is shown in FIG. 1 a schematic representation of a system constructed in accordance with the principles of the present invention, and designated generally as 100. System 100 preferably includes a catheter 101, a controller unit 102, and a cryogenic fluid supply 103. The system 100 may also include, although the operation of the overall device and invention does not so require, a user interface or console 104 coupled to the controller unit 102. The controller unit 102 is preferably composed of any number of suitable mechanical or electronic device components that are capable of receiving and executing programmed instructions, sensor signals, or manual user input as is known in the art. The controller unit 102 may comprise, without limitation, any of the following components: (i) a computer or microprocessor, (ii) a flow pump and vacuum pump, (iii) a filter or fluid filtration system, (iv) a feedback, closed-loop, or open-loop control system, including all mechanical and electrical components customarily used in such control systems, (v) any number of pressure and temperature sensors, or (vi) any of the commonly used devices for controllably dispensing and receiving fluid flows in a closed-loop flow system wherein mass flow rate, temperature and pressure of the fluid flow is monitored and regulated.

As shown in FIG. 1, the controller unit 102 is coupled to the flow of cryogenic fluid from the cryogenic fluid supply 103, wherein the controller unit 102 then directs and regulates the flow of cryogenic fluid into the catheter 101. During application of the device, the distal portion of the catheter 101 is introduced into a body and the distal tip 105 of the catheter 101 is placed in contact with or proximate to selected tissue. Cryogenic fluid is then directed to flow to the distal tip 105, whereupon the fluid undergoes a gas dynamic expansion and evaporation process, thereby cooling the distal tip 105 to low temperatures for selectively cold-treating surrounding tissue.

The cryogen supplied may be either in a liquid or a gaseous state. The cryogen is cooled and/or compressed to a predetermined initial temperature and initial pressure before introduction into the catheter 101. The catheter 101 contains multiple tubes (not shown), preferably made of flexible or rigid material such a polymer, fiber, metal, or any combination thereof. The tubes are arranged to create a plurality of lumens (not shown) for the flow of cryogen therethrough. These lumens are arranged to create a closed-loop circulation path for the flow of cryogen through the device. This includes an injection lumen (not shown) through which the cryogen is introduced into the catheter 101 to flow from the supply 103 through to the distal tip 105; and a return lumen (not shown), through which cryogen eventually flows back to the controller unit 102 from the distal tip 105. The controller unit 102 is used to create vacuum pressure conditions (or negative gauge pressure) at the proximal portion of the return lumen. The initial supply pressure of the cryogen is preferably on the order of 30 to 40 atmospheres, or 400 to 600 psia, much higher than the eventual final pressure in the vacuum return lumen. The resultant negative pressure gradient drives the high pressure cryogen drawn from supply 103 to flow through an injection lumen in catheter 101, to the distal tip 105, and thereafter to flow back through the return lumen.

Figure 2:
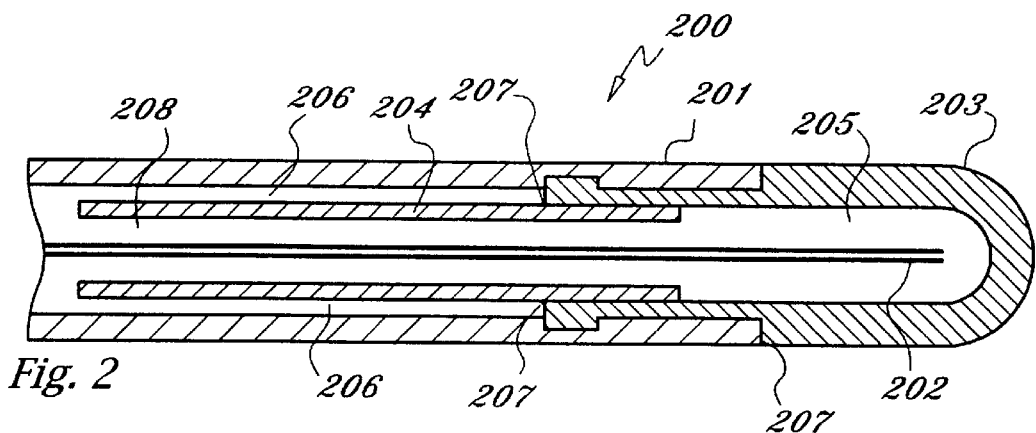
FIG. 2 is a longitudinal cross-sectional view of the distal portion of the device shown in FIG. 1, taken along line 2—2.

FIG. 2 shows a longitudinal cross-sectional view of an exemplary embodiment of the present invention, illustrating, namely, the distal end portion of catheter 101, and referred to generally as catheter 200. Referring now to FIG. 2, the distal end portion of catheter 200 comprises a catheter outer tube 201, an injection tube 202, a distal tip 203, a restriction tube 204, an expansion chamber 205, a vacuum buffer layer 206, seals 207, and a return lumen 208. The injection tube 202 is disposed inside of the outer tube 201 and tip 203, thereby defining a space occupied by the expansion chamber 205 at the distal end of catheter 200, and the return lumen 208 at all points proximal from the distal tip. The restriction tube 204 is coupled proximate the tip 203, and extends longitudinally parallel to the interior surface of the outer tube 201, thereby defining the vacuum buffer layer 206 therebetween. Tip 203 is adhesively coupled to the outer tube 201 by seals 207. Such seals 207 also couple restriction tube 204 to tip 203.

The outer tube element 201 circumferentially encloses injection tube 202 and restriction tube 204, wherein all elements are coaxially disposed with respect to each other, such that a longitudinal centerline (not shown) of outer tube 201 coincides with the longitudinal centerline of both injection tube 202 and restriction tube 204. Restriction tube 204 is preferably an annularly shaped body, having a radial symmetry equivalent to that of the outer tube 201 and injection tube 202. However, it is emphasized that the foregoing spatial arrangement of elements 201, 202 and 204 are but one particular arrangement, and that any number of alternative arrangements may be used so as to provide for the suitable operational characteristics of the present invention, as more fully explained below.

Restriction tube 204 is disposed in proximity to the interior surface of outer tube 201. The longitudinal position of restriction tube 204 is preferably on the order of one to five catheter diameters proximate from the very distal end of tip 203. The longitudinal length of restriction tube 204 is preferably on the order of three to twenty catheter diameters, thereby defining a vacuum buffer layer 206 of similar corresponding longitudinal dimension.

All of tubes 201, 202, and 204 are preferably made of solid material, such as polyimide, or other polymer, metal, or combination thereof, suitable for the transport of high pressure fluids, as is well known to those skilled in the art. The tip 203 is made of a material that is thermally transmissive. The tip 203 is constructed out of any of the well-known thermal conductors such as Group IB or IIB metals, or other materials with similar thermal conductivity and transmissivity properties, as is well-known to those skilled in the art. Although numerous materials and structures may be thermally conductive or thermally transmissive at very low temperatures, as used herein, a "thermally-transmissive" element is intended to broadly encompass any element that readily conducts heat across a broad range of temperatures, such as from 50 to 500 K.

The tip 203 is coupled to the distal end portion of outer tube 201 through adhesion provided by seals 207. It is understood that any number of adhesion or coupling mechanisms or devices may be used for seals 207, preferably including, but not limited to, a glue, epoxy, or other suitable coupling agent, as is well known to those skilled in the art. Alternatively, outer tube 201 and tip 203 may be formed as a single element, such that the use of seals 207 to couple the two elements is not necessary.

The "cooling" power of the device is centered around the expansion chamber 205 inside tip 203. As shown in FIG. 2, tip 203 circumferentially encloses the absolute distal end portion of injection tube 202, thereby defining the expansion chamber 205 therebetween. During operation of the device, cryogen flows through the injection tube 202 and exits into expansion chamber 205. Cryogen flowing through the injection tube 202 is in mixed liquid and gas phase, at several dozen atmospheres pressure and at a temperature equal to or below standard room temperature. Upon injection into the expansion chamber 205, the cryogen undergoes two thermodynamic changes: (i) a positive Joule-Thomson throttling process, which may be substantially isenthalpic, but acts to substantially lower the pressure and the temperature of gaseous cryogen; and (ii) a liquid to vapor phase change, wherein the resultant enthalpy of vaporization is absorbed by the cryogen. The dual effects of the Joule-Thomson throttling and vaporization of the cryogen comprise the overall cooling mechanism of the device. The so-called "cooling power" of the device is accordingly a direct function of these thermodynamic changes, and, in particular, is positively correlated to (i) the "quality" of the cryogen supplied, i.e. the relative percentage of the cryogen which is in vapor rather than liquid phase, (ii) the relative high pressure of the cryogenic fluid supplied, and (iii) the mass flow rate of the cryogenic fluid supplied. If any of the foregoing criteria are diminished, the overall "cooling power" of the device is degraded.

The corresponding gas dynamic expansion and evaporation of the supplied high-pressure cryogenic fluid in the near field of the expansion chamber 205 creates a net flow of low temperature fluid through the expansion chamber 205. This flow of low temperature fluid in the near field of the tip 203 causes the temperature of the tip 203 to drop to levels significantly below that of ambient body temperatures, through convective and conductive heat transfer between the tip 203 and the cryogen flow in expansion chamber 205. The low temperature tip 203 may then be applied to contact a region of tissue so as to selectively freeze or "cold-treat" the tissue for medical and surgical applications.

The resulting low pressure, low temperature cryogen gas flows from the expansion chamber 205 through the return lumen 208, which extends through to the proximal end of catheter body 200. Upon reaching the proximal end of the catheter 200, the "spent" cryogen is: (i) vectored back to the controller unit or cryogen supply (not shown) for recycling of the cryogen in a closed-loop flow arrangement, or (ii) discarded from the device in an open-loop flow arrangement.

Upon exiting the injection tube 202 and flowing throughout the return lumen 208, the flow properties of the cryogen must be regulated to provide for optimal operation of the device. The device may be operated at various cryogen flow rates. Generally, the cooling power of the device is positively correlated to the cryogen flow rate, which in turn is negatively correlated to the temperatures achieved in the expansion chamber 205. In particular, the device may used for two specific applications: (i) for "mapping", wherein the cryogen flow rate is relatively low and the temperature in the distal tip region is relatively high, and (ii) for ablation, wherein the cryogen flow rate is relatively high and the temperature in the in the distal tip region is relatively low. "Mapping" entails the application of the device to tissue at temperatures which will not burn or destroy living tissue, but that will induce an electro-cardial signal detectable by a standard electrocardiogram device monitoring such tissue. This in turn enables the user of the device to navigate the catheter throughout tissue regions so as to place the device at the desired location. For ablation, the device is operated at maximum cooling power wherein tissue may be cold-treated using very low temperatures, as opposed the relatively high "mapping temperature." In a preferred embodiment of the invention, the cryogen flow rate preferably ranges from 1000 to 2000 standard cm$^3$/min. For "mapping", the corresponding temperature of the expanded cryogen in the expansion chamber 205 is approximately −10 degrees Centigrade at a flow rate of 1000 standard cm$^3$/min., while for ablation the temperatures range as low as −130 degrees Centigrade for flow rates up to 1900 standard cm$^3$/min.

Additionally, the pressure of the cryogen flowing through the return lumen 208 must conform to the structural limitations of the catheter body 200. The cryogen must be contained within the device and cannot be allowed to leak into the surrounding environment. As such, the device must maintain its structural integrity and fluid impermeability. In a typical application of the device, these structural constraints and operating limitations dictate that the static pressure in return lumen 208 be maintained below atmospheric pressure. The static pressure inside the return lumen 208 is regulated by the controller unit 102 (not shown), which, as stated above, also regulates the pressure of the cryogen supplied into the injection tube 202. By regulating the controller unit to provide a vacuum (less than 14.7 psia) pressure in the return lumen, the cryogen is effectively (i) contained within the catheter body 200, and (ii) is drawn to flow from the distal end of catheter 200 back to the proximal end and thus "circulates" through the device.

However, as enumerated above, the cooling power of the device is dependent upon achieving the maximum possible pressure and flow rate of cryogen in the expansion chamber 205. Thus, the pressure therein may be fine-tuned to provide for better performance while still operating within the overall structural limitations of the device. Indeed, the supplied cryogen flows through the distal end of the injection tube 202 and exits into the expansion chamber 205 at a pressure significantly higher than the operating static pressure within the proximal portion of the return lumen 208. This higher pressure in the expansion chamber 205 is effectively maintained by the presence of restriction tube 204 inside of the distal portion of the return lumen 208, just "downstream" of the expansion chamber 205.

As the cryogen flows through the return lumen 208, it experiences head losses due to friction, turbulence, and other energy transport mechanisms present in most flow conduits, as is well known to those skilled in the art. Although the head of a fluid flow is generally a measure representative of the sum of its kinetic, potential and pressure energies, the term "head loss", as used herein, shall generally be positively correlated to a decrease in both static and dynamic pressure of the cryogenic fluid flow as it flows through the device. The presence of the restriction tube 204 inside of the return lumen 208 just proximate the tip 203 causes additional such head losses, which would otherwise be absent if such restriction tube 204 were not included in the device. Upon entering the restriction tube 204 at its distal opening, the cryogen experiences a "sudden contraction loss" in head, defined as head losses which occur when there is an abrupt decrease in conduit size. Upon exiting the restriction tube 204 at its proximal end, the cryogen experiences a "sudden expansion loss" in head, defined as head losses which occur when there is an abrupt increase in conduit size.

The flow inside of the return lumen 208, including that portion of the lumen inside of the restriction tube 204, is generally turbulent and compressible. As the cryogen flows from the expansion chamber 205 through the restriction rube 204 in into the return lumen 208, as explained above, head losses contribute to an increase in static pressure of such cryogen.

A commonly used mathematical tool for calculating the head losses in small conduits, for incompressible flow, is the Darcy-Weisbach model. According to the Darcy-Weisbach formula, the head loss occurring in such conduits is calculated as follows: lost head=$f(L/d)(V^2/2\ g)$, where $f$ is the friction factor, L is the conduit length, d is the conduit diameter, V is the flow velocity, and g is the acceleration due to gravity. For incompressible flow, the mass flow rate of cryogen is proportional to $Vd^2$. Thus for a given cooling power, and hence a given mass flow rate, the overall proportionality of lost head is as follows: lost head $L/d^5$.

This however, is strictly applicable to incompressible flow only. However, although the flow is compressible, empirical evidence has shown that if the overall static pressure change is no more than 40% from one flow to another flow point, the Darcy-Weisbach model for the incompressible flow of a fluid in a closed conduit may be used for compressible flow conditions. Empirical evidence has shown that this pressure differential may be applicable for the flow of cryogen through the restriction tube 204. Although the pressure differential is not always under 40%, under certain conditions, it approaches that value. Nevertheless, the overall proportionality obtained above holds for compressible flow, in that the head losses are directly proportional to length, and inversely proportional to diameter.

Thus, the overall head loss (and hence the pressure in the expansion chamber 205) in the catheter 200 may be fine-tuned with a high degree of sensitivity be alternatively placing restriction tubes of various diameter and length inside of the return lumen 208. In this embodiment, for a standard 7 French catheter, the length of the restriction tube 204 is preferably between 0.50 cm and 125 cm, respectively, while the inside diameter of the return lumen 208 proximate the restriction tube 204 is preferably between 0.025 cm and 0.125 cm.

Thus, the net effect of cumulative head losses from sudden contraction and expansion losses, as well as the relative smaller diameter of the restriction tube 204 from that of the return lumen 208, results in significantly higher pressures in the expansion chamber 205 for any given mass flow rate of cryogen through the device. For example, at "mapping" flow rates of 1000 standard cm$^3$/min., the static pressure in the expansion chamber 205 may be in the range of approximately 12+ psia, while the static pressure in the return lumen 208 may be in the range of about 8 psia. At ablation flow rates of 1900 standard cm$^3$/min., the static pressure may be in the range of 17 psia in the expansion chamber 205 and 14 psia in the return lumen 208.

Another challenge which arises under "mapping" conditions is that for low static pressures, typically 12 psia or lower, the cryogen in the expansion chamber 205 may reach its solid-liquid-vapor phase triple point, thereby affecting the temperature stability of the fluid cryogen. To prevent this, the pressure in the expansion chamber must be maintained at a level sufficiently high enough to prevent the cryogen from reaching its triple point. Thus, the presence of the restriction tube 204 enables the device to be operated at lower flow rates and temperatures while maintaining the static pressure above the triple point in the expansion chamber 205. The restriction tube effectively functions as a pressure choking mechanism, while also enabling the fine-tuning of the pressure of the cryogen near the distal tip 203, thereby broadening the operational applicability of the device. In effect, the device has a high pressure resistance tip with a correspondingly higher cooling power than would be achieved using conventionally designed catheter devices which lack such a restriction tube mechanism.

In addition, because the tip 203 is coupled to the restriction tube 204 by seals 207, the bending strength of the distal end of catheter 200 is enhanced. If the catheter 200 were to be kinked at its distal end, the cryogen flow would have to penetrate both (i) the seals 207 bonding the restriction tube 204 with the tip 203, and (ii) the seals 207 bonding the tip 203 with the outer tube 201. This double sealed tip design provides for extra protection from leakage and enhances the bending strength of the device structure.

During operation of the device, the catheter 200 is typically introduced into a body that is a source of ambient heat, thereby warming the cryogen flowing therethrough and producing significant head losses in the flow of high pressure cryogen in the injection tube 202, and thus degrading the overall cooling power of the device. However, low temperature cryogen flowing through the return lumen 208 convectively "sub-cools" the high pressure cryogen flowing through the injection tube 202. This conductive sub-cooling is enhanced by the increased flow velocity of the cryogen in the restriction tube 204, thereby counteracting the warming effects of the aforementioned ambient heat sources surrounding the distal end of catheter 200, where such effects are the most detrimental to the cooling power of the device.

The warming effects of ambient heat sources around the distal end of catheter 200 are also counteracted by the vacuum buffer layer 206, which is an annular space defined between the inner surface of outer body 201 and the outer surface of restriction tube 204. As shown in FIG. 2, the longitudinal length of vacuum buffer layer 206 is approximately equal to the length of the restriction tube 204. Because the proximal end of vacuum buffer layer 206 is in fluid communication with the return lumen 208 just "downstream" from the restriction tube 204, the pressure in vacuum buffer layer 206 is at or below atmospheric pressure due to the vacuum provided by the controller unit (not shown). As shown in FIG. 2, the distal end of the vacuum buffer layer 206 is sealed by seals 207, so that cryogen flowing through return lumen 208 upon exiting restriction tube 204 is directed to flow away from the vacuum buffer layer 206. This creates a region of relative rarefaction which serves to insulate the cryogen flowing coaxially within the restriction tube 204 and vacuum buffer layer 206, thereby further enhancing the cooling power of the device by preventing ambient heat from warming the cryogen flow in either of the return lumen 208 enclosed by restriction tube 204, or the injection tube 202 enclosed by such portion of the return lumen 208.

Figure 3:
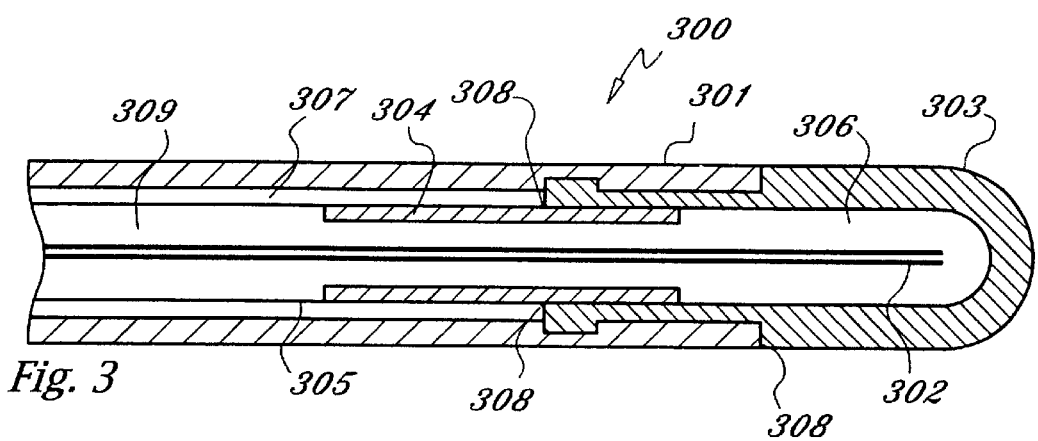
FIG. 3 is a longitudinal cross-sectional view of the distal portion of an alternate arrangement of the device which is part of the system shown in FIG. 1.

Another exemplary embodiment of the present invention is illustrated in FIG. 3. FIG. 3 displays the distal end portion of a catheter body, labeled generally as 300, including a catheter outer body 301, an injection tube 302, a tip 303, a sleeve 304, a restriction tube 305, a expansion chamber 306, a vacuum buffer layer 307, a plurality of seals 308, and a return lumen 309. Cryogen is supplied through the injection tube 302, whereupon it is injected into the expansion chamber 306. The tip 303 is coupled to the outer body 301 and the sleeve 304 with seals 308. In this embodiment of the present invention, the overall spatial arrangement of the injection tube 302, tip 303, and restriction tube 305 in the distal portion of the catheter 300 is substantially the same as in the corresponding elements displayed in the embodiment of FIG. 2.

However, as displayed in FIG. 3, a sleeve 304 is coupled to the proximal end of tip 303 and the distal end of restriction tube 305. The proximal end of restriction tube 305 is not shown in FIG. 3, although the length of restriction tube 305 extends longitudinally for approximately 3 to 20 catheter diameters within return lumen 309. Restriction tube 305 may also be detachably coupled to sleeve 304, such that restriction tubes of varying length and diameter may be used to regulate the pressure drop due to head losses occurring in the flow of cryogen therethrough, as more specifically discussed above. The sleeve 304 is preferably constructed out of a metal or metal alloy, such that it provides sufficient strength to maintain the structural integrity of the tip assembly of catheter 300. As discussed above, the presence of the sleeve 304 with seals 308 serves to prevent the cryogen flow from leaking out of the device and reinforces the overall bending strength of the distal portion of the catheter 300.

Figure 4:
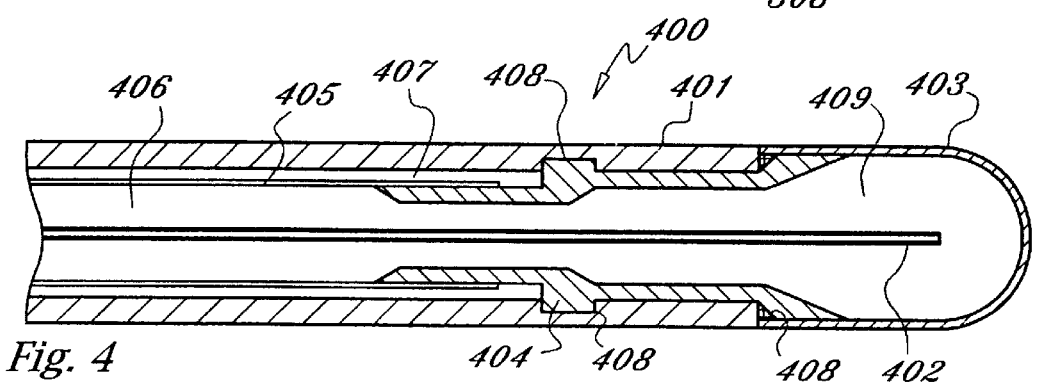
FIG. 4 is a longitudinal cross-sectional view of the distal portion of another configuration of the device which is part of the system shown in FIG. 1.

Still another exemplary embodiment of the invention is shown in FIG. 4. FIG. 4 shows the distal end portion of catheter 400, which includes an outer body 401, an injection tube 402, a tip 403, a sleeve 404, a restriction tube 405, a return lumen 406, a vacuum buffer layer 407, a plurality of seals 408, and an expansion chamber 409. In this embodiment, sleeve 404 is structurally fitted to the outer tube 401 and tip 403. The use of multiple seals 408 to bond all of elements 401, 403 and 404 provides increased structural rigidity and pressure strength to the catheter 400, thereby allowing for greater mass flow through the device, and hence, greater cooling power is achieved.

Sleeve 404 may be manufactured from a metal or metal alloy, or any suitable material having a relatively high modulus of elasticity as well as sufficient tensile, compressive, and shear strength to withstand the operating pressures of the device. The sleeve 404 is coupled to the tip 403, which is in turn coupled to the outer body 401 by the seals 408. The interior geometry of the sleeve 404 is tapered as shown in FIG. 4, thereby providing for successive cross-sections of varying area in the distal end portion of return lumen 406. As high pressure cryogen exits the injection tube 402 into the expansion chamber 409, the resultant low pressure, low temperature cryogen flows through the return lumen 406 and is successively vectored through the "throat" of the sleeve 404, such "throat" being the longitudinal position within the return lumen where the cross-sectional area of the return lumen, as dictated by the geometry of the sleeve 404, is smallest. The tapered flow of cryogen through the sleeve 404 further accelerates the low pressure cryogen flow through the return lumen 406, thereby causing "gradual" (as opposed to sudden) contraction and expansion head losses, as is well known to those skilled in the art. These head losses may also be utilized to further fine-tune the pressure drop in the cryogen flow from the tip 403 through the return lumen 406. Furthermore, the sleeve 404 may be composed of a thermally conductive material and coupled to the tip 403, so that the flow of low temperature cryogen through the sleeve 404 further creates additional net heat transfer from the tip 403 to the cryogen flowing through the return lumen 406. This enhances the "cooling power" of the device beyond that contemplated and discussed in the previous embodiments.

All of the various components of the present invention, including all elements (other than the tips 203, 303, 403, and sleeves 304 and 404) disclosed in FIGS. 2–4, are constructed from polyimide or some other suitable polymer based material, having sufficient rigidity to enable the effective operation of the device. Other materials which may be used include Teflon® brand tubing and coatings, polyurethane, silicone, or nylon.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device comprising:
    a first member defining an injection lumen,
    a second member circumferentially disposed around the first member, to define a return lumen therebetween, the return lumen having proximal and distal ends and at least one cross-sectional area therebetween, the proximal end of the return lumen being in fluid communication with a source of vacuum, and
    a third member disposed around a distal end portion of the return lumen between the second member and the first member to define a restriction lumen between the third member and the first member, the restriction lumen having at least one cross-sectional area smaller than the at least one cross-sectional area of the return lumen, the third member further defining a vacuum buffer lumen between the second member and the third member, the vacuum buffer lumen being in fluid communication with the return lumen.

2. The device according to claim 1, further comprising a supply of cryogenic fluid in fluid communication with the injection lumen.

3. The device according to claim 2, further comprising:
    a controller unit, said controller unit regulating the flow rate, temperature and pressure of the supply of cryogenic fluid, said controller unit being fluidly coupled to the first and second members, said controller unit controllably dispensing the cryogenic fluid through the injection lumen and controllably receiving the cryogenic fluid from the return lumen.

4. The device according to claim 2, wherein the cryogenic fluid is nitrous oxide.

5. The device according to claim 1, further comprising a tip member having an outer surface and an inner surface, the tip member:
    (i) being coupled to the distal end of the second member;
    (ii) circumferentially enclosing the distal end of the return lumen; and
    (iii) defining an expansion volume between the distal end portion of the first member and the inner surface of the tip member, the expansion volume being disposed to occupy the distal end portion of the return lumen.

6. The device according to claim 5, wherein the tip member is in part composed of a thermally-transmissive material.

7. The device according to claim 5, wherein the third member further comprises a distal orifice and a proximal orifice, the distal orifice being in fluid communication with the expansion volume, the restriction lumen being disposed between the distal orifice and the proximal orifice, creating a pressure drop therebetween when a fluid flow is applied through the restriction lumen.

8. A medical device comprising:
    an elongate injection tube having
        a proximal end portion having at least one proximal orifice, and
        a distal end portion having at least one distal orifice,
    an elongate catheter tube circumferentially disposed around the injection tube and defining a return lumen therebetween, the return lumen being in fluid communication with a source of vacuum, the catheter tube having a distal end portion, the distal end portion being coupled to a thermally transmissive element, the thermally transmissive element circumferentially enclosing the distal end portion of the injection tube, and
    a restriction tube circumferentially disposed inside of the catheter tube and enclosing a distal end portion of the return lumen proximate the thermally transmissive element
    wherein the restriction tube is circumferentially disposed inside of the catheter tube to define an annular space therebetween, the annular space having:
        a distal end proximate the thermally transmissive element, and
        a proximal end in fluid communication with the return lumen.

9. The device according to claim 8, further comprising a supply of cryogenic fluid in fluid communication with the proximal end portion of the injection tube, thereby defining a fluid path through the at least one proximal orifice, the injection tube and the at least one distal orifice.

10. The device according to claim 9, wherein the cryogenic fluid is nitrous oxide.

11. The device according to claim 9, wherein the cryogenic fluid is carbon dioxide.

12. The device according to claim 8, wherein the thermally transmissive element further comprises:
    a first axis of radial symmetry substantially parallel to the injection tube and catheter tube,
    a distal end portion, the distal end portion having a spherically curved surface, the surface having a circular axis of symmetry co-linear with the first axis, the surface being disposed to define an expansion chamber proximate the orifice,
    a proximal end portion, the proximal end portion having at least one ridged surface, the ridged surface being sealably coupled to the distal end portion of the catheter tube.

13. The device according to claim 8, wherein the return lumen comprises a distal end portion, and further comprising:
- a sleeve element coupled to the catheter tube, the sleeve element being disposed around a distal end portion of the return lumen and having
  - a distal end portion, the distal end portion being coupled to the thermally transmissive element, and
  - a proximal end portion, the proximal end portion being coupled to the restriction tube.

14. The device according to claim 13, wherein the sleeve element is coaxially disposed around the injection tube to define an annular space, the annular space having a longitudinal axis substantially parallel to the injection tube, the distal end portion of the return lumen being partially occupied by the annular space, the annular space having:
- a distal cross-sectional area substantially perpendicular the longitudinal axis, and
- a proximal cross-sectional area substantially perpendicular the longitudinal axis,
- wherein the distal cross-sectional area is greater than the proximal cross-sectional area.

15. The device according to claim 13, wherein the sleeve element is an axisymmetric annular body, circumferentially disposed around the distal end portion of the injection tube, having an interior surface coterminous with the distal end portion of the return lumen, the sleeve element having:
- a distal inner diameter; and
- a proximal inner diameter proximate from the distal inner diameter,
- wherein the distal inner diameter is greater than the proximal inner diameter.

16. A method for cooling a cryogenic medical device, including the steps of:
- a) providing a supply of cryogen at a pressure of at least two atmospheres absolute pressure in a storage container;
- b) fluidly connecting said supply of cryogen with a catheter having a first lumen inside of a second lumen, and a thermally transmissive element;
- c) providing a flow regulation system to dispense cryogen into the first lumen and to reduce the pressure in the second lumen to below one atmosphere absolute pressure;
- d) controllably injecting said supply of cryogen through the first lumen in proximity to the thermally transmissive element; and
- e) providing a third lumen inside of the second lumen, the third lumen being proximal to the thermally transmissive element, the third lumen having a cross-sectional area smaller than the cross-sectional area of the second lumen.

17. The method according to claim 16 wherein the cryogen is nitrous oxide.

18. The method according to claim 16 wherein the cryogen is carbon dioxide.

* * * * *

UNITED STATES PATENT AND TRADEMARK OFFICE
CERTIFICATE OF CORRECTION

PATENT NO.   : 6,589,234 B2
DATED        : July 8, 2003
INVENTOR(S)  : Jean-Pierre Lalonde et al.

It is certified that error appears in the above-identified patent and that said Letters Patent is hereby corrected as shown below:

<u>Title page,</u>
Item [56], References Cited, U.S. PATENT DOCUMENTS, add
-- 5,524,116  A  10/1993        Baust, et al……………..606/23 --

Signed and Sealed this

Eighteenth Day of November, 2003

JAMES E. ROGAN
*Director of the United States Patent and Trademark Office*